United States Patent
Arad

(10) Patent No.: US 7,096,061 B2
(45) Date of Patent: Aug. 22, 2006

(54) APPARATUS FOR MONITORING CHF PATIENTS USING BIO-IMPEDANCE TECHNIQUE

(75) Inventor: Shimon Arad, Tel-Aviv (IL)

(73) Assignee: Tel-Aviv University Future Technology Development L.P., Tel-Aviv (IL)

( * ) Notice: Subject to any disclaimer, the term of this patent is extended or adjusted under 35 U.S.C. 154(b) by 0 days.

(21) Appl. No.: 10/189,161

(22) Filed: Jul. 3, 2002

(65) Prior Publication Data

US 2004/0006279 A1    Jan. 8, 2004

(51) Int. Cl.
  *A61B 5/05* (2006.01)
(52) U.S. Cl. .................................. 600/547; 702/65
(58) Field of Classification Search ........... 600/547; 128/920; 702/19, 57, 65
  See application file for complete search history.

(56) References Cited

U.S. PATENT DOCUMENTS

| | | | |
|---|---|---|---|
| 5,311,878 A | 5/1994 | Brown et al. | |
| 5,746,214 A | 5/1998 | Brown et al. | |
| 5,749,369 A | 5/1998 | Rabinovich et al. | |
| 5,788,643 A | 8/1998 | Feldman | |
| 6,387,671 B1 * | 5/2002 | Rubinsky et al. | 435/173.7 |
| 2003/0126630 A1 | 7/2003 | Jersey-Willuhn et al. | |

FOREIGN PATENT DOCUMENTS

GB   2 138 148   10/1984

OTHER PUBLICATIONS

Rosenfeld, M. et al.; "Numerical Solution of the Potential Due to Dipole Sources in Volume Conductors With Arbitrary Geometry and Conductivity;" Jul. 1996; IEEE Transactions on Biomedical Engineering; vol. 43 No. 7; pp. 679-689.

Abboud, S. et al.; "Numerical Calculation of the Potential Distribution Due to Dipole Sources in a Spherical Model of the Head;" 1994; Computers and Biomedical Research; vol. 27; pp. 441-455.

Barber, D.C.; "A Review of Image Reconstruction Techniques for Electrical Impedance Tomography;" Mar./Apr. 1989; Med. Phys.; vol. 16, No. 2; pp. 162-169.

Charach, G. et al.; "Transthoracic Monitoring of the Impedance of the Right Lung in Patients with Cardiogenic Pulmonary Edema;" Year 2001; Crit. Care Med.; vol. 29, No. 6; pp. 1137-1144.

Dong, G. et al.; "Derivation from Current Density Distribution to Conductivities Based on the Adjoint Field Theory and Numerical Test With Finite Volume Method"; The $2^{nd}$ Japan, Australia and New Zealand Joint Seminar, Jan. 24-25, 2002, Kanazawa, Japan Applications of ElectroMagnetic Phenomena in Electrical and Mechanical Systems; 8 pages.

Edwardson, M. et al.; "A Bioelectrical Impedance Analysis Device for Improved Management of Congestive Heart Failure;" Year 2000; Computers in Cardiology; vol. 27; pp. 9-12.

Eyuboglu, B. M. et al.; "In Vivo Imaging of Cardiac Related Impedance Changes;" Mar. 1989; IEEE Engineering in Medicine and Biology Magazine; vol. 8, No. 1; pp. 39-45; XP 00002279.

(Continued)

*Primary Examiner*—Ruth S. Smith
(74) *Attorney, Agent, or Firm*—Fenster & Company

(57) ABSTRACT

A method is described for generating an impedance image of the chest, in which electrical data of the chest is acquired, and a finite volume method is used to calculate an impedance image from the electrical data, using an analytical expression for the Jacobian.

15 Claims, 6 Drawing Sheets

OTHER PUBLICATIONS

Govreen-Segal, D. et al.; "Real-Time PC-Based System for Dynamic Beat-to-Beat QT-RR Analysis;" Year 1999; Computers and Biomedical Research; vol. 32; pp. 336-354.

Hoetnik, A. E. et al.; "Comparing Spot Electrode Arrangements for Electric Impedance Cardiography"; Physiol. Meas. 23 (2002); Apr. 8, 2002; pp. 457-467.

Imhoff, M. et al.; "Noninvasive Whole-Body Electrical Bioimpedance Cardiac Output and Invasive Thermodilution Cardiac Output in High-Risk Surgical Patients"; Crit Care Med 2000, vol. 28, No. 8; Copyright 2000; pp. 2812-2818.

Lucquin, B. et al.; "Finite Differences in Time and Finite Volumes in Spcae;"1998; Introduction to Scientific Computing; Section 7.8; John Wiley & Sons; pp. 300-304.

Newell, J. C. et al.; "Assessment of Acute Pulmonary Edema in Dogs by Electrical Impedance Imaging"; Feb. 1996; IEEE Transactions on Biomedical Engineering; vol. 3, No. 2; pp. 133-138.

Raajmakers, E. et al.; "The Influence of Extravascular Lung Water on Cardiac Output Measurements Using Thoracic Impedance Cardiography"; Physiol. Meas. 19 (1998); Aug. 27, 1998; pp. 491-499.

Record, P.M. et al.; "Multifrequency Electrical Impedance Tomography;" Year 1992; 11815 Clinical Physics and Physiological Measurement; vol. 13, Supplement A; pp. 67-72.

Riu, P. et al.; "In Vivo Static Imaging for the Real and the Reactive Parts in Electrical Impedance Tomography Using Multifrequency Techniques;" Oct. 29, 1992; IEEE; pp. 1706-1707; XP 00514393.

Shahidi, A. V. et al.; "Impedance Tomography: Computational Analysis Based on Finite Element Models of a Cyclinder and a Human Thorax;" 1995; Annals of Biomedical Engineering; vol. 23; pp. 61-69.

Subramanyan, R. et al.; "Total Body Water in Congestive Heart Failure—A Pre and Post Treatmetn Study;" Sep. 1980; Jour. Asso. Phys. Ind.; vol. 28; pp. 257-262.

Versteeg, H. K. et al.; "An Introduction to Computational Fluid Dynamics-The Finite Volume Method", Chapter 2 "Conservation Laws of Fluid Motion and Boundary Conditions"; Longman Scientific & Technical, 1995; pp. 10-40.

* cited by examiner

RESPIRATION

RAW ECG DATA

RR SIGNAL

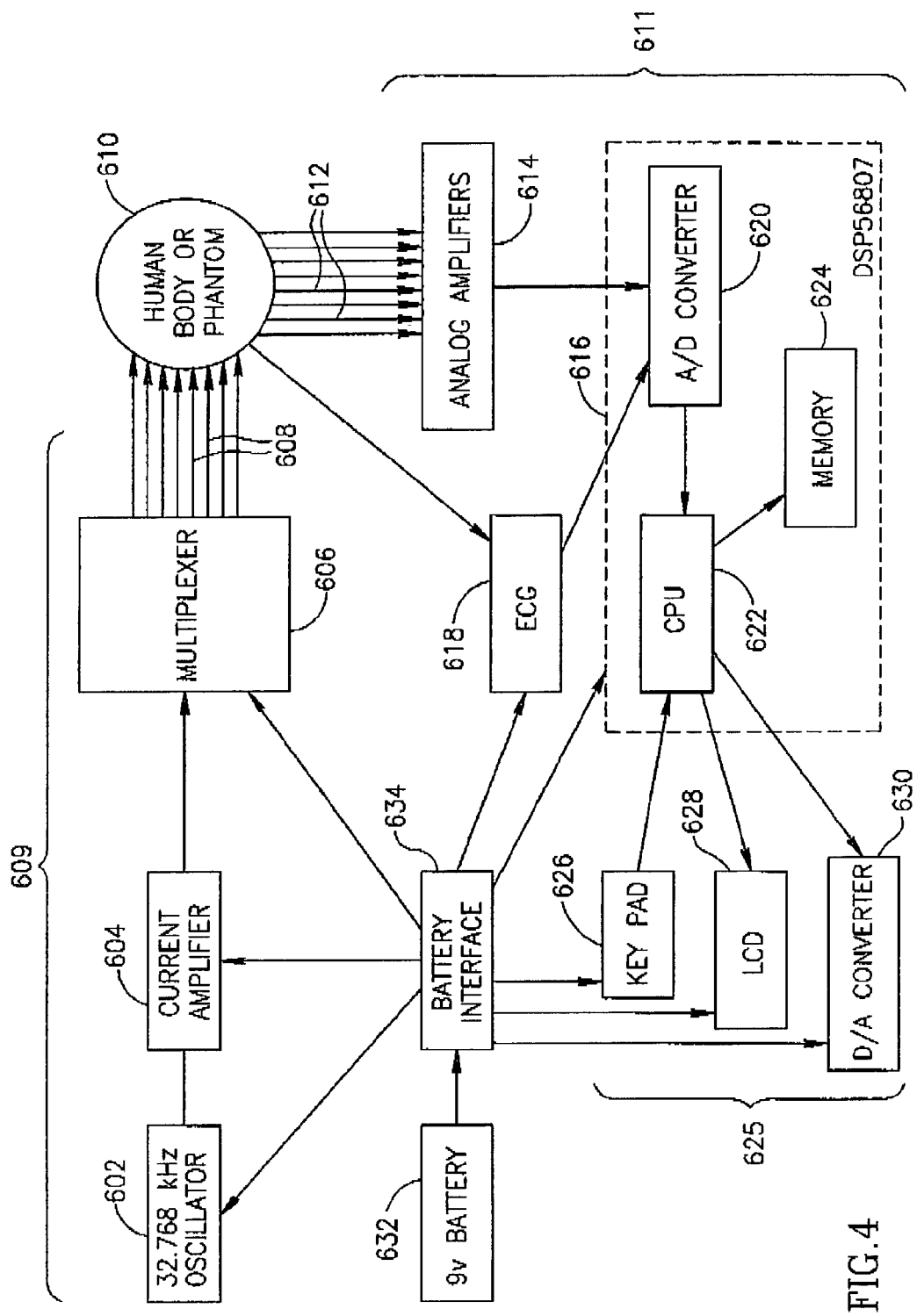

APPARATUS FOR MONITORING CHF PATIENTS USING BIO-IMPEDANCE TECHNIQUE

FIELD OF THE INVENTION

The present invention relates to the field of instrumentation for monitoring and evaluating patients with heart disease, particularly congestive heart failure.

BACKGROUND OF THE INVENTION

Congestive heart failure (CHF) is a condition in which the heart does not adequately maintain circulation of blood. It is characterized by an increase in retained body water, especially extracellular water, often in the lungs (pulmonary edema). A decrease in extracellular fluid in CHF patients typically indicates an improvement in heart performance. Conventional methods of monitoring CHF patients either require expensive equipment and trained personnel (e.g. measuring pulmonary artery and central venous pressure with catheters, measuring blood flow through the mitral annulus and pulmonary veins with doppler echocardiography) or are not very accurate (e.g. monitoring changes in body weight, observing neck vein distension, measuring ankle dimensions). Impedance measurements of the chest, both resistive and reactive (capacitive) impedance, have been shown to correlate with total body water, extracellular body water, and the ratios of these quantities to fat free mass (U.S. Pat. No. 5,788,643). Monitoring trends in these quantities in congestive heart failure patients is a particularly useful way to determine whether medication doses need to be increased or decreased. As stated in U.S. Pat. No. 5,788,643: "Subramanyan, et al. and others have shown that both the resistive and reactive components of the body's impedance to the flow of relatively high frequency (50 kHz) electrical current is sensitive to the amount of fluid retained by a patient with CHF. As the CHF resolves, resistance and reactance both increase as does the [ratio of reactance to resistance]. See Subramanyan, et al., "Total Body Water in Congestive Heart Failure," Jour. Asso. Phys. Ind., Vol. 28, September, 1980, pages 257–262. . . . It would be most desirable to provide a simple way of detecting increases in body water of patients with CHF before hospitalization is necessary and permitting adjustments in medication and/or diet in time to prevent an episode of acute heart failure." The patent describes a figure of merit, calculated from impedance measurements, for deciding when medical intervention may be needed for a CHF patient.

There are several parameters that affect the impedance of the thorax. The impedance of the chest cavity is small compared to changes in the impedance of the skin, and chest cavity impedance changes substantially during the respiratory cardiac cycle, due to the changing volume of air in the lungs, and during the cardiac cycle due to the changing blood perfusion of the lungs. Various techniques are used to separate out the part of the impedance due to excess body water, and to meaningfully compare such impedance measurements taken in the same patient on different days. For example, U.S. Pat. No. 5,749,369, and Charach, G. et al., "Transthoracic Monitoring of the Impedance of the Right Lung in Patients with Cardiogenic Pulmonary Edema," Crit. Care Med. 2001, Vol. 29, No. 6, pages 1137–1144 discuss ways to compensate for drifting skin impedance.

In addition to the techniques used in bulk measurements of impedance, impedance imaging is also useful for separating out the different contributions to the impedance. In impedance imaging, a set of many electrodes (usually 16 or 32) is placed on the body, for example encircling the chest, and the voltage is measured at each electrode, while a known current is applied between different pairs of the electrodes. The resulting data is used to produce a map of the internal impedance of the body, using various mathematical techniques, some of them similar to those used in x-ray tomography. Some image reconstruction techniques are described in a review paper by D. C. Barber, Med. Phys., (1989), Vol. 16, pages 162–169.

The finite element method, finite difference method, and boundary element method are different techniques used to solve differential equations numerically. Solving Poisson's equation to find the potential distribution in the body due to known current sources and impedance distribution, together with boundary conditions, is known as the forward problem. These numerical methods are used in the field of bio-impedance to solve the forward problem. Rosenfeld, M. et al., "Numerical Solution of the Potential Due to Dipole Sources in Volume Conductors With Arbitrary Geometry and Conductivity," IEEE Transactions on Biomedical Engineering, July 1996, Vol. 43, No. 7, pages 679–689 use a different technique, the finite volume method, to solve the forward problem. Finding the impedance distribution with known potential distribution at the surface (measured with surface electrodes, for example), and known current sources (flowing from one surface electrode to another), is called the inverse problem. Some of the inverse problem solvers use the forward problem solver as a step in an iterative solution.

An early paper on impedance imaging by Eyuboglu, B. M. et al., "In Vivo Imaging of Cardiac Related Impedance Changes," March 1989, IEEE Engineering in Medicine and Biology Magazine, Vol. 8, pages 39–45 discusses the use of gating and time-averaging to separate out the contributions of the respiratory and cardiac cycles to the chest impedance and impedance images, including impedance images of pulmonary embolisms. The authors state, "[T]he resistivity of most tissue changes significantly with blood perfusion into the tissue . . . . [I]t has been shown that the thoracic resistivity changes during the cardiac cycle can be imaged by ECG-gated EIT [electrical impedance tomography] . . . . The average resistivity of lung tissue increases with the amount of air inspired . . . [by] approximately 300 percent . . . from maximal expiration to maximal inspiration . . . . The resistivity of lung tissue also changes with the perfusion of blood following ventricular systole . . . . This change has been calculated as 3 percent . . . [which] may be as small as the noise level . . . . Therefore, to pick up the cardiac-related resistivity variations within the thorax during normal breathing, the respiratory component and the noise must be eliminated . . . . The respiratory component may be rejected by temporal averaging . . . . Experience has shown that averaging over at least 100 cardiac cycles is needed during shallow breathing to attenuate the respiratory component and to improve S/N ratio. Cardiac gating is required . . . . " Brown and Barber develop numerical methods to reduce noise in U.S. Pat. No. 5,311,878, and they use differences in impedance at different electrical frequencies between 10 kHz and 600 kHz to distinguish between cardiac and respiratory effects in U.S. Pat. No. 5,746,214. Newell, J. C. et al., "Assessment of Acute Pulmonary Edema in Dogs by Eletrical Impedance Imaging," February 1996, IEEE Transactions on Biomedical Engineering, Vol. 43, No. 2, pages 133–138 demonstrate the use of impedance imaging to detect pulmonary edemas in dogs, and discuss the variability in impedance over time and from day to day, which makes it difficult to measure long-term changes.

SUMMARY OF THE INVENTION

An aspect of some embodiments of the invention concerns the use of an electrocardiograph (ECG) to measure the depth, frequency, and/or timing of the breathing cycle, in order to be able to correct for the effect of breathing on the chest impedance, which would otherwise mask the effects of pulmonary edema and other symptoms of congestive heart failure on the chest impedance. The breathing cycle is correlated with the RR Intervals extracted from ECG data, because breathing modulates the heart's pacemaker located at the sinuatrial node. Breathing depth also affects the amplitude of the raw ECG data, since the higher impedance of the chest when the lungs are expanded reduces the voltage at the ECG electrodes. By tracking changes in the ECG data at a given point in the cardiac cycle, for example the minimum voltage or the maximum voltage between electrodes during each cardiac cycle, the breathing cycle can be monitored. Although the breathing cycle can also be monitored directly, by measuring air flow into and out of the lungs, this requires more patient cooperation than taking ECG data does, and requires extra equipment, so it is easier to monitor breathing by using ECG data ECG data is usually obtained anyway in impedance imaging, in order to monitor the cardiac cycle, and no extra equipment is needed if the ECG data is used to monitor the breathing cycle at the same time. Optionally, the system is adapted to be used as home monitoring system, with the information transferred to a remote location where a physician views and diagnoses the condition of a patient. The data can be transferred, for example, by a modem over telephone lines, through secure broadband internet fines, or by another means of communication.

An aspect of some embodiments of the invention concerns solving the inverse problem, i.e. calculating an impedance image of the chest from measured voltages between different pairs from a set of electrodes on the surface of the body, using the finite volume method. The finite volume method offers several advantages over the finite element method and boundary element method for solving the inverse problem, but it has not previously been used for solving the inverse problem in impedance imaging.

An aspect of some embodiments of the invention concerns using ECG data, together with impedance imaging, to evaluate the condition of a congestive heart failure patient, for example in order to determine whether to increase or decrease doses of medication. Diuretics, for example, which are prescribed to reduce pulmonary edema and other symptoms of congestive heart failure, may induce cardiac arrhythmia if taken in too high a dose. In determining the optimal dose, patient outcome is likely to be better if treatment is determined by looking at the overall picture, including symptoms of congestive heart failure and symptoms that may indicate incipient arrhythmia, as well as other symptoms that may be seen in ECG data, rather than simply starting or stopping medication based on isolated symptoms. U.S. Pat. No. 5,788,643 describes a figure of merit for deciding when medical intervention is called for in a CHF patient, but this figure of merit is based only on impedance measurements, not on ECG data.

Optionally, the ECG data is also used to measure the breathing cycle to correct the impedance imaging, as described above. Optionally, the electrodes used for the ECG are also used for the impedance imaging.

There is thus provided, in accordance with an embodiment of the invention, a method for generating impedance images of the chest, comprising:
  acquiring electrical data of the chest;
  obtaining electrocardiograph data of a patient;
  analyzing the electrocardiograph data to obtain information about breathing parameters at the time the electrical data was acquired; and
  reconstructing at least one impedance image of the chest from the electrical data and the information about breathing parameters;
  wherein the information about breathing parameters reduces the sensitivity of the at least one impedance image to breathing parameters.

Optionally, reconstructing at least one impedance image comprises:
  reconstructing at least one preliminary impedance image of the chest from the electrical data; and
  correcting the at least one preliminary impedance images to form the at least one impedance image, taking into account the breathing parameters.

Optionally, analyzing the electrocardiograph data comprises analyzing changes in RR intervals.

Alternatively or additonally, analyzing the electrocardiograph data comprises analyzing changes in a voltage measured at a same phase in each cardiac cycle.

Alternatively or additionally, analyzing the electrocardiograph data comprises analyzing the average over one or more cardiac cycles of a voltage measured by the electrocardiograph.

In an embodiment of the invention, reconstructing at least one preliminary image comprises reconstructing a plurality of preliminary images, and correcting the at least one impedance images comprises sorting the preliminary images into a plurality of bins according to the breathing parameters.

Optionally, sorting the preliminary images into bins comprises sorting according to the state of expansion of the lungs.

Alternatively or additionally, sorting the preliminary images into bins comprises sorting according to the elapsed time since the last maximum expansion of the lungs.

Alternatively or additionally, sorting the preliminary images into bins comprises sorting according to the elapsed time since the last minimum expansion of the lungs.

Optionally, sorting the preliminary images into bins comprises sorting according to a cardiac volume.

Alternatively or additionally, sorting the preliminary images into bins comprises sorting according to a heart rate.

Alternatively or additionally, sorting the preliminary images into bins comprises sorting according to a phase of the cardiac cycle.

In an embodiment of the invention, acquiring the electrical data comprises gating by the cardiac cycle.

Optionally, correcting the at least one preliminary impedance images comprises averaging the impedance data acquired over one or more breathing cycles.

Alternatively or additionally, reconstructing at least one preliminary image comprises reconstructing a plurality of preliminary images for which the impedance data was acquired at a plurality of phases in the breathing cycle, and correcting the at least one preliminary impedance images comprises averaging the preliminary impedance images.

Optionally, the method includes measuring the air flow into the lungs, and calibrating the information about breathing parameters obtained from the electrocardiograph using said measured air flow.

Alternatively or additionally, the method includes measuring the air flow out of the lungs, and calibrating the information about breathing parameters obtained from the electrocardiograph using said measured air flow.

Optionally, reconstructing at least one preliminary impedance image of the chest comprises using a finite volume method.

There is further provided, according to an embodiment of the invention, a method for generating an impedance image of the chest, comprising:

acquiring electrical data of the chest; and using a finite volume method to calculate an impedance image from the electrical data.

Optionally, the method includes:

formulating an initial impedance image;

using a finite volume method to calculate an expected set of electrical data if the impedance distribution of the chest matched the initial impedance image;

determining a difference between the acquired electrical data and the expected electrical data; and calculating a new impedance image based on said difference.

Optionally, calculating an expected set of electrical data and calculating a new impedance image are iterated at least one time, using the new impedance image calculated in at least one previous iteration to calculate the expected set of electrical data in each iteration except the first iteration.

Optionally, calculating an expected set of electrical data and calculating a new impedance image are iterated until the difference between the acquired electrical data and the expected set of electrical data is small enough to satisfy a stopping condition.

Optionally, calculating the new impedance image comprises calculating with a Newton-Raphson method.

Alternatively or additionally, calculating the new impedance image comprises calculating with a modified Newton-Raphson method.

In an embodiment of the invention, formulating the initial impedance image comprises ascribing typical impedances to different parts of the chest according to at least one image of the chest.

Optionally, ascribing impedances according to at least one image of the chest comprises ascribing impedances according to at least one x-ray image.

Optionally, ascribing impedances according to at least one x-ray image comprises ascribing impedances according to at least one x-ray computed tomography image.

Alternatively or additionally, ascribing impedance according to at least one image of the chest comprises ascribing impedances according to at least one magnetic resonance image.

Alternatively or additionally, ascribing impedances according to at least one image of the chest comprises ascribing impedances according to at least one ultrasound image.

In an embodiment of the invention, using the finite volume method comprises inverting a matrix with a technique that is adapted for inverting sparse matrixes.

Optionally, inverting a matrix comprises inverting a matrix with the successive over relaxation method.

Optionally, acquiring electrical data of the chest comprises measuring potentials at a plurality of locations on the body, while known currents are applied at a plurality of locations on the body.

There is further provided, in accordance with an embodiment of the invention, a method for monitoring a congestive heart failure patient, comprising:

generating at least one impedance image of the patient's chest;

acquiring electrocardiograph data of the patient; and calculating a parameter characterizing medical treatment of the patient, from electrocardiograph data and at least one impedance image of the chest.

Optionally, calculating at least one parameter comprises calculating a recommended dose of a medication.

Optionally, calculating a recommended dose of medication comprises calculating a recommended dose of a diuretic.

Optionally, using the electrocardiograph data comprises using the QT interval.

Optionally, using the QT interval comprises using the QT interval to detect hypokalemia.

Alternatively or additionally, using the electrocardiograph data comprises using the U wave amplitude.

Optionally, using the U wave amplitude comprises using the U wave amplitude to detect hypokalemia.

There is further provided, in accordance with an embodiment of the invention, an apparatus for making corrected impedance images of the chest, comprising:

an impedance imaging data acquisition system which acquires impedance imaging data of the chest;

an electrocardiograph which obtains electrocardiograph data of a patient; and a data analyzer which analyzes the electrocardiograph data to obtain information about breathing parameters at the time the impedance imaging data was acquired, and reconstructs, from the impedance imaging data and the information about breathing parameters, at least one impedance image of the chest with reduced sensitivity to breathing parameters.

There is further provided, in accordance with an embodiment of the invention, an apparatus for making impedance images of the chest, comprising:

an impedance imaging data acquisition system which acquires impedance imaging data of the chest;

a data analyzer which reconstructs an impedance image of the chest from said impedance imaging data, using a finite volume method.

BRIEF DESCRIPTION OF THE DRAWINGS

Exemplary embodiments of the invention are described in the following sections with respect to the drawings. The drawings are generally not to scale. Features found in one embodiment can also be used in other embodiments, even though not all features are shown in all drawings.

FIG. 4 is a schematic drawing of a hardware configuration for impedance imaging, according to an exemplary embodiment of the invention;

DETAILED DESCRIPTION OF EXEMPLARY EMBODIMENTS

Aspects of some embodiments of the invention concern improved systems for making impedance images of the chest, and for using these images to monitor congestive heart failure patients. In order to describe the embodiments of the invention shown in FIGS. 2–5, it will be convenient to first describe some prior art shown in FIG. 1. The various options described for FIG. 1 are also options for the embodiments of the invention shown in FIGS. 2–5.

Figure 1:
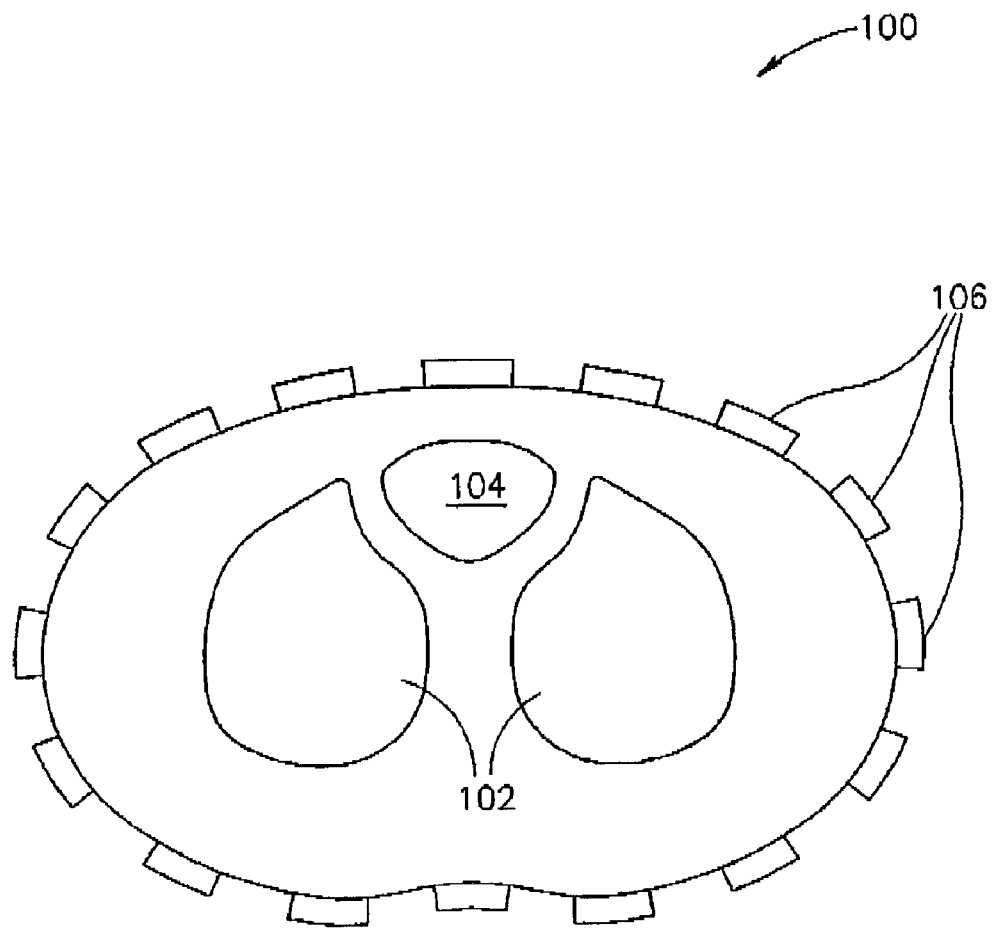
FIG. 1 is schematic view of a cross-section of the chest, showing the placement of electrodes for impedance imaging, according to prior art.

FIG. 1 shows a cross-section of a chest 100, including lungs 102 and a heart 104. Sixteen electrodes 106 are shown placed on the skin all around the chest. The number of electrodes used is optionally great enough to obtain a desired resolution in the impedance image, but not so great that the measurements and data analysis take too long. Sixteen and thirty-two are numbers that are commonly used, but other numbers of electrodes may be used. To take a set of data for an impedance image, current is first passed through two of the electrodes, and the voltage is measured at all of the electrodes. Then another pair of electrodes is chosen for passing current through, and the process is repeated for many different pairs of electrodes. Optionally, the voltage is not measured on the electrodes with current passing through them, since for those electrodes the voltage tends to be dominated by the voltage drop between the electrode and the skin, so it is difficult to obtain accurate potential measurements on those electrodes. Optionally, more than one pair of electrodes has current passing through it, for one or more of the measurements. In this case, different electrodes optionally have different currents flowing through them. Although this may make the data analysis simpler, it has the disadvantage that there are more electrodes for which it is difficult to get good potential measurements. Optionally, one or more of the electrodes are also used to obtain ECG data.

In FIG. 1, the electrodes are arranged in a single circle around the body, similar to the arrangement used by Eyuboglu, Brown and Barber (loc. cit.). This arrangement may not provide any information about the axial distribution of impedance inside the body, but provides a two-dimensional cross-sectional map of impedance, a weighted average over the axial direction of the three-dimensional impedance distribution. Optionally, the electrodes are arranged not in a single circle, but in two or more circles at different axial positions. Such a two dimensional grid of electrodes provides data for constructing a three-dimensional map of impedance. More than one circle of electrodes is optionally used for other reasons as well. For example, optionally the positive electrode supplying current is always located in one circle, and the negative electrode with current is always in the other circle. This arrangement provides more independent measurements than if the positive and negative electrodes were chosen from the same circle of electrodes, since in that case switching the two electrodes would not provide any new information. Having one circle of electrodes for potential measurements, and one or two separate circles of electrodes for supplying current, also avoids the problem of measuring potential on an electrode that is supplying current.

Typical currents used for impedance imaging are 1 to 5 milliamps. A current of this magnitude is not dangerous, but is high enough to provide a reasonable signal to noise ratio when measuring the voltage. In order to obtain reactive (capacitive) impedance data as well as resistance data, the currents optionally are AC, typically at frequencies between 10 kMz and several hundred kHz. However, lower frequencies may also be use. For safety reasons, DC current is typically not used in medical procedures, even if reactive impedance data is not needed. Reactive impedance is related to the capacitance of cell membranes, and resistive impedance is related to the volume of water. Because low frequency currents cannot penetrate the cell membranes, low frequency resistive impedance tends to measure only the volume of extracellular water, while high frequency resistive impedance measures the volume of water within cells as well.

Figure 2:
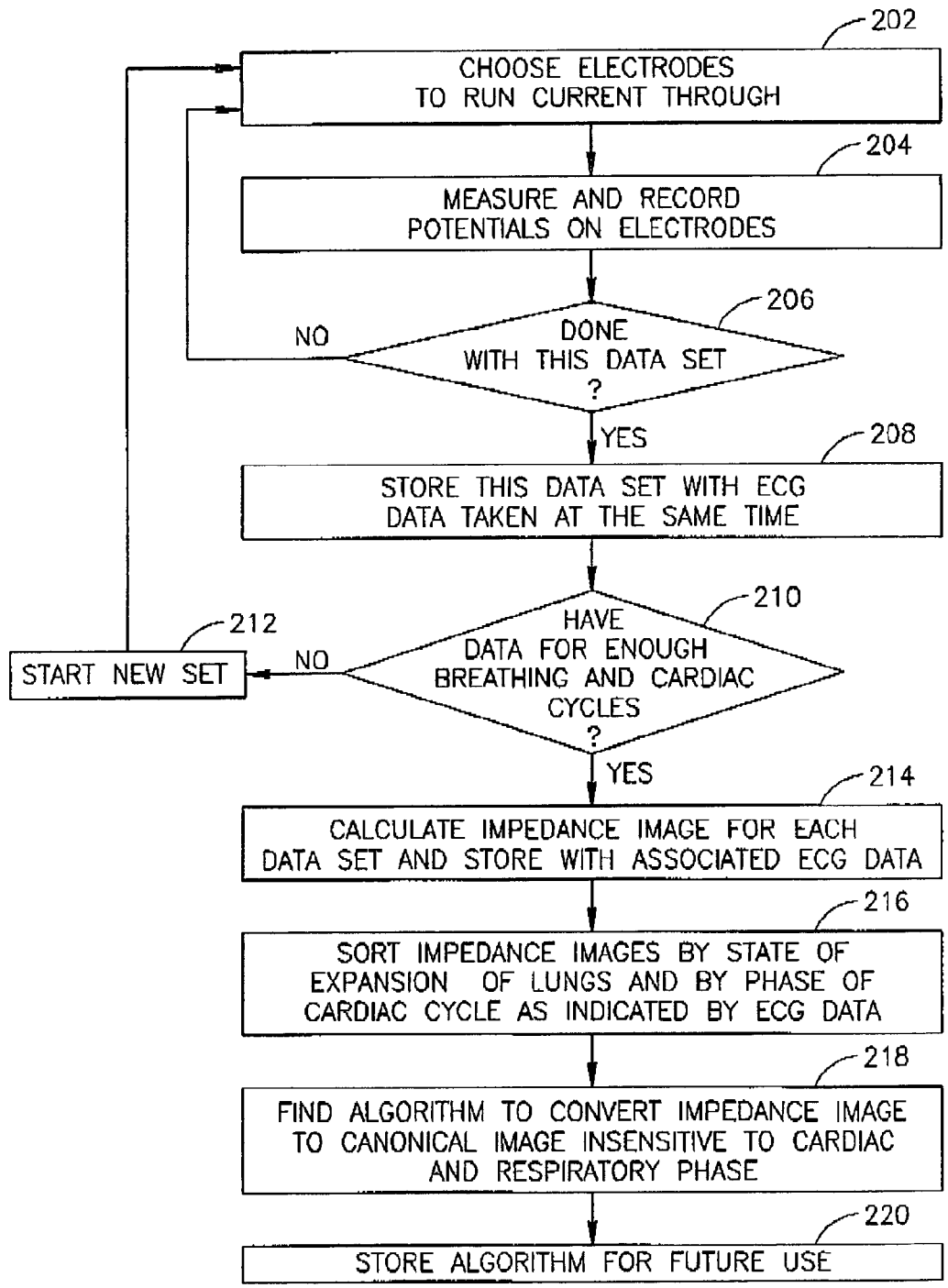
FIG. 2 is a flowchart showing how ECG data is used to distinguish the effect of breathing from the effect of the cardiac cycle on an impedance image of the chest according to an exemplary embodiment of the invention.

FIG. 2 is a flowchart describing a procedure for using ECG data to monitor the state of expansion of the lungs, and to calibrate impedance images of the chest according to the state of expansion of the lungs. Using this procedure, it may be possible to detect the relatively small changes in impedance associated with changes in thoracic fluid volume, in spite of the larger changes in impedance associated with breathing.

At 202, a pair of electrodes is chosen to apply current. At 204, the voltage is measured and recorded on each electrode, while current is flowing through the chosen electrodes. Optionally, as discussed above, the voltage is not measured on the electrodes carrying current, or certain electrodes are dedicated to carrying current and other electrodes are dedicated to measuring the potential. At 206, the flow goes back to 202 and another pair of electrodes is chosen to carry current, until data has been taken with every possible pair of electrodes, or until it is decided, based on some criterion, that a sufficient set of data has been taken. The potential data is then stored at 208, together with ECG data taken at the same time. At 210, the procedure goes to 212, and a new set of potential measurements is initiated, until it is decided that a sufficient number of data sets have been taken. Optionally, data sets are taken at intervals short compared to the cardiac cycle time, and data is taken over a period corresponding to several breathing cycles, at least. This allows the impedance images to be correlated with the cardiac and breathing cycles. At 214, after all the data has been taken, an impedance image is computed for each data set, and associated with the ECG data taken at the same time. Optionally, the image is computed using the finite volume method, according to the procedure detailed below in the description of FIG. 4.

At 216, the impedance images are sorted by the phase of the cardiac cycle, and by the state of expansion of the lungs, as indicated by the ECG data taken at the same time the impedance data was measured for that image. The state of expansion of the lungs is optionally inferred from one or both of two different features of the ECG data. When the lungs are in a more expanded state, the RR interval increases, since the expansion of the lungs affects the heart's pacemaker located at the sinuatrial node. Optionally, in using the RR interval to infer the state of expansion of the lungs, variations in the RR interval at frequencies much lower than the breathing frequency are filtered out, since these could be due to other factors which affect the RR interval, for example stress. In addition, the expansion of the lungs increases the resistive impedance of the chest, and this reduces the voltage measured by the ECG electrodes. Normally, in ECG systems, the raw voltage signals are adjusted by pre-amps, which compensate for the slow changes in voltage associated with the breathing cycle, which are not usually of interest. In order to use this aspect of the ECG data to monitor breathing, the pre-amps may be bypassed.

Optionally, the state of expansion of the lungs as inferred from ECG data is calibrated by direct measurements of lung expansion, for example by measuring the air flow into and/or out of the lungs. Optionally, the impedance images are also sorted into bins by the rate of expansion or contraction of the lungs, or other characteristics of the breathing that may affect the impedance image, especially the appearance of pulmonary edemas in the impedance image. If the heartbeat is irregular in strength or timing, then the images are also optionally sorted by systolic volume, interval of ventricular contraction, and other characteristics of the heartbeat that may affect the impedance image.

At 218, the sorted impedance images are converted to a canonical impedance image in which the appearance of pulmonary edema, or the measured thoracic fluid volume, is independent of the cardiac and breathing cycles. At 220, the canonical image is stored. Such a canonical image may be used to meaningfully compare thoracic fluid volume, or other characteristics of a pulmonary edema, at different times, hours or days or weeks apart, and to detect trends which may indicate the need to increase or decrease doses of medication, or to stop or start a given medication, or to intervene medically in other ways.

Optionally, instead of computing preliminary impedance images at 214 and ten sorting them at 216, the data sets are sorted at 216, with or without some preliminary processing, and the sorted data sets are used to produce a canonical impedance image at 218. Since the data sets contain the information used to produce the preliminary images, it should be understood that any manipulations performed on the preliminary images to produce a corrected image might instead be performed directly on the data sets without first producing preliminary images.

Several different concepts may optionally be used, singly or in any combination, in processing the images to produce a canonical image:

1. Averaging the images in a given bin (for example, the images taken at a given state of expansion of the lungs, and a given phase of the cardiac cycle), and then taking a linear combination of images in different bins.
2. The coefficients of this linear combination may be negative. For example, if the change in impedance of the lungs associated with a pulmonary edema is correlated with the cardiac cycle, then images taken at one phase in the cardiac cycle may be subtracted from images taken 180 degrees apart in the cardiac cycle. Such a procedure may emphasize pulmonary edemas in the resulting canonical image, and de-emphasize other features of chest impedance that are not of interest.
3. Changes in chest impedance at the breathing frequency, which are likely not to be of interest, are eliminated or reduced by averaging over bins that represent different phases in the breathing cycle, at the sane phase in the cardiac cycle.
4. Converting an image taken at any state of lung expansion to an equivalent image at a canonical state of lung expansion, for example with the lungs fully expanded, or the lungs emptied, or half-way in between. An algorithm which does this could make use of a series of impedance images taken at different states of expansion of the lungs.

Optionally, the algorithm for producing a canonical impedance image is adjusted for the particular patient based on previous data taken for that patient. Additionally or alternatively, the algorithm is based on previous data taken from one or more other patients, possibly from a large number of other patients.

Figure 3A:
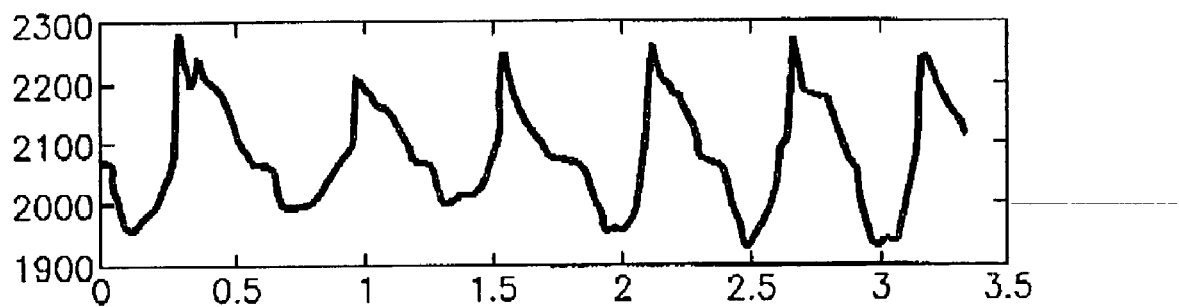
FIGS. 3A, 3B and 3C show breathing data and ECG data, illustrating how the ECG data is affected by breathing.
Figure 3B:
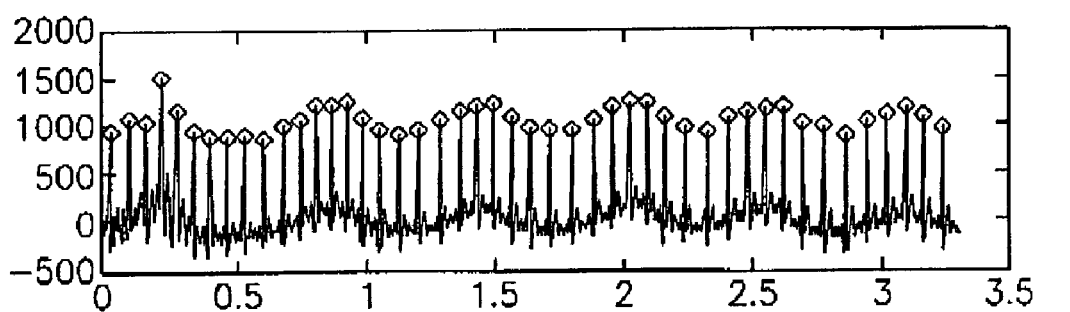
Figure 3C:
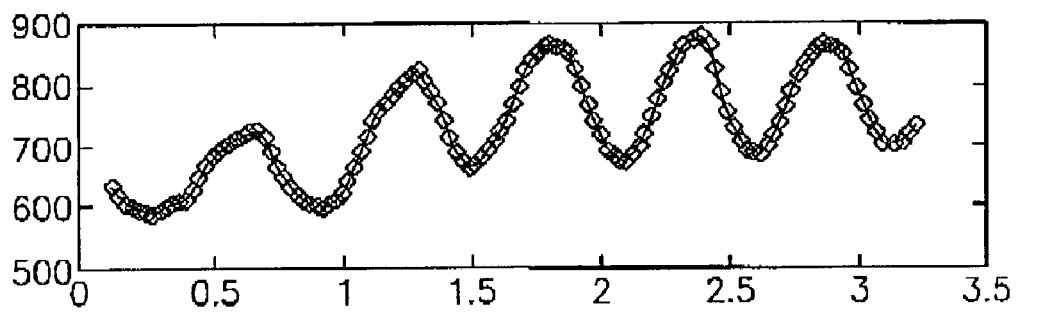

FIG. 3A shows lung volume as a function of time for six breathing cycles, FIG. 3B shows the raw ECG data, and FIG. 3C shows RR interval derived from the ECG data, plotted for the same time period. When the lungs are more expanded, the chest impedance is greater, and the voltage at the ECG electrodes is lower. Hence there is a negative correlation between ECG voltage and lung volume. The RR interval is also correlated negatively with lung volume, because respiration affects the pacemaker of the heart in the sinuatrial node. The correlations between lung volume, raw ECG voltage, and RR interval are strong enough so that ECG voltage and RR interval may be usefully used to monitor the state of expansion of the lungs during breathing.

FIG. 4 schematically shows a hardware configuration for an impedance imaging system which uses ECG data to determine breathing parameters, in accordance with an embodiment of the invention. The hardware comprises a current injection module 609, a potential measuring and processing module 611, and a user interface module 625. In the current injection module, a 32.768 kHz oscillator 602 generates a stable sinusoidal current of a few micro-amperes, which is amplified to the desired current, 1 to 5 milliamperes, by current amplifier 604. A dual 1-to-4 multiplexer 606 is used to inject the current through any desired pair chosen from 8 electrodes 608, which are placed around the thorax of a human body 610, or around a phantom. Potential measuring and processing module 611 includes eight electrodes 612, which are applied to the thorax and sense voltage, analog amplifiers 614, and a Motorola DSP56807 chip 616. An electrocardiogram 618 also feeds voltage measurements into chip 616. Chip 616 includes an analog to digital convertor 620 which converts the analog voltage data to digital form, a central processing unit 622, and a memory 624. The digital data is stored in the memory, for each pair of electrodes used to inject current and is then used by the CPU to reconstruct an impedance image. The CPU also uses the data from the ECG to calculate parameters such as RR and QT intervals, which are used to infer breathing parameters. User interface module 625 includes a keypad 626 used to enter data or feedback from the user into the CPU, a liquid crystal display 628 for presenting the results or for giving instructions to the patient during the measurement process, and a digital to analog convertor 630 for plotting data during development of the system. A 9 volt battery 632 provides power for all three modules, via a battery interface 634, which provides positive and negative voltage and a ground.

Optionally, user interface module 625 is located remotely, with the data transmitted (for example, over phone lines with a modem, or over a secure broadband internet connection), or user interface module 625 includes hardware for transmitting the impedance imaging data from memory 624 to a remote location. Optionally, current amplifier 604 and multiplexer 606 are also controlled remotely, or they are controlled by a computer, optionally chip 616, which is programmed to inject a given sequence of currents through the different electrodes. These options may be useful, for example, for monitoring the condition of a patient who is at home, without the need for him to come into a hospital every time.

Figure 5:
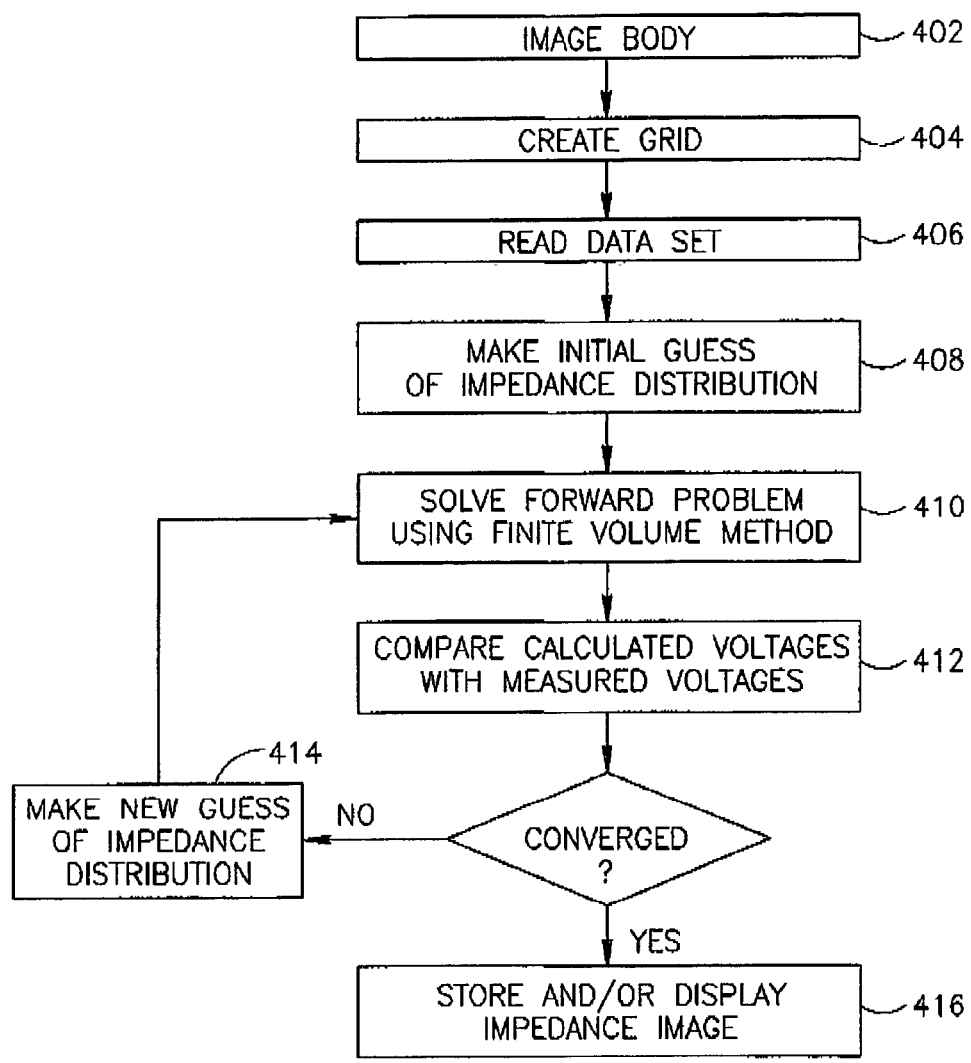
FIG. 5 is a flowchart showing how the finite volume method is used to calculate an impedance image, according to an exemplary embodiment of the invention.

FIG. 5 is a flowchart outlining how the finite volume method is used to calculate an impedance image from the potential data taken with different pairs of electrodes carrying current. Initially, in 402, an image is made of the chest of the patient, using, for example, magnetic resonance imaging, computerized x-ray tomography, or ultrasound. Alternatively, with some loss of accuracy, the patient's chest is modeled by some standard body model, perhaps parameterized by characteristics such as weight, height gender, and body type. Optionally, the model or image includes the whole body, or more of the body, rather than just the chest, which makes it possible to more accurately account for current paths that are not confined to the chest.

At 404, the chest or body model is used to create a three-dimensional grid. Optionally, the grid conforms to the surface of the body. Optionally, the grid conforms to the surfaces of the lungs and/or the heart, which generally have substantially different impedance from other parts of the chest, and from each other. Optionally, the grid changes during the breathing cycle and heart beat, so that it can continue to conform to the surfaces of the lungs and heart. Alternatively, the grid conforms only to some approximate average surfaces of the lungs and heart, or does not conform to the surfaces of the lungs and heart at all. The grid coordinates of the various electrodes (including their orientations and outlines, as well as their positions) are determined and stored.

In 406, potential data is read at each electrode, for each pair of current-carrying electrodes, as described above in the description of FIG. 1 and FIG. 2. In 408, an initial guess is made of the impedance distribution of the chest, for example, using information about the location of the lungs and heart obtained from the image made in 402, and/or from a chest model used in 402. Optionally, the initial guess for the impedance distribution simply assigns typical values of impedance for lung tissue, cardiac tissue, and the rest of the chest cavity.

In 410, the finite volume method is used to solve the forward problem, calculating the expected surface potential at each electrode where voltage is measured, for each choice of current carrying electrodes, using the initial guess for impedance distribution as a starting point. The finite volume method uses the integral form of Poisson's equation, which becomes a set of simultaneous linear equations when Poisson's equation is discretized and the integral is replaced by a sum. The boundary conditions for Poisson's equation are Neumann-type conditions, stating the current flux normal to the boundary. The finite volume method is more accurate than the finite element method, the most commonly used method in the field of bio-impedance, at solving Poisson's equation with Neumann boundary conditions, because it can treat discontinuous impedance distributions and discontinuous current sources (B. Lucquin and O. Pironneau, *Introduction to Scientific Computing*, John Wiley & Sons, 1998, pp. 300–304). The finite volume method also makes more efficient use of computational resources and CPU time than the finite element method Abboud, S. et al, Comput. Biomed. Res., (1994), Vol. 27, pages 441–455. The set of linear equations can be represented in sparse matrix form, and relaxation methods can be used that are very fast and efficient for sparse matrixes, for example the successive over relaxation (SOR) method.

In 412, the surface potential calculated at each electrode in 410, for each chosen pair of current-carrying electrodes, is compared to the voltages measured at each electrode in 406. If difference between the measured and calculated potentials is small enough, then the initial guess made in 408 for the impedance distribution is a good match to the actual impedance distribution. Otherwise, the Newton-Raphson method or a similar method may be used in 414 to make an improved guess for the impedance distribution, and step 410 (solving the forward problem) is repeated, using the new guess. The Newton-Raphson method involves differentiating (finding the Jacobian of) the matrix associated with the set of linear equations in 410, with respect to changes in the impedance distribution. Here the finite volume method offers another advantage over the finite element method, since the finite volume method allows the matrix elements to be expressed symbolically in terms of the impedance distribution, and the expressions can be mathematically manipulated to find their derivatives, and hence the Jacobian. With the finite element method, on the other hand, the matrix is found only in numerical form, and finding the Jacobian is then much more time consuming, for a large matrix.

The Newton-Raphson method involves inverting a matrix, called the Hessian matrix, which depends on the Jacobian and on the difference between the measured and calculated potentials. Because the Hessian matrix is often ill-conditioned, the Newton-Raphson method may be unstable. Optionally, the stability of the convergence is improved by using a modified Newton-Raphson method, for example the Marquardt method. These methods involve adding to the Hessian matrix a regularization matrix, which makes it better conditioned.

At each iteration of the loop shown in FIG. 4, the calculated potential is compared to the measured voltages on the electrodes. When the difference between them is small enough, the latest guess for the impedance distribution is accepted as a good approximation to the actual impedance distribution. In 416, this impedance distribution is stored, and optionally displayed on a monitor or printed.

Figure 6:
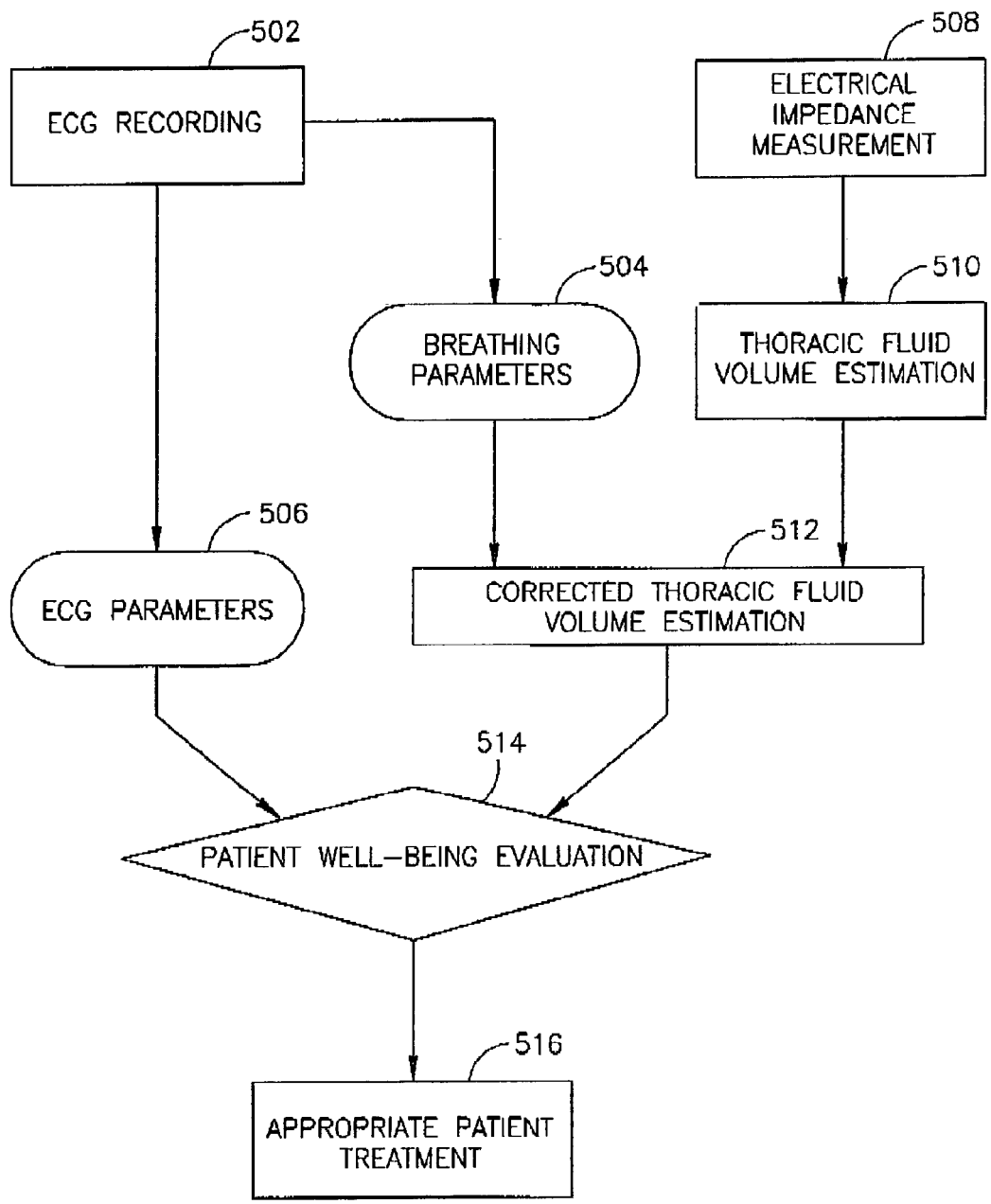
FIG. 6 is a flowchart showing how ECG data and impedance images are used to assess the condition of a congestive heart failure patient, according to an exemplary embodiment of the invention.

FIG. 6 is a flowchart showing how impedance imaging is combined with ECG data to produce an overall evaluation of a patient suffering from congestive heart failure, and to decide on appropriate treatment. ECG data is recorded in 502. This data is used both for determining breathing parameters in 504, as described above in FIG. 2, and for detecting problems with heart function, for example arrhythmia or incipient arrhythmia, in 506. At the same time, in 508, impedance imaging is used to estimate the thoracic fluid volume in 510, and this estimate is adjusted by taking into account the breathing parameters determined in 504. This leads in 512 to a canonical impedance image, as discussed above in FIG. 2, which characterizes the thoracic fluid volume, and the presence of pulmonary edema, independently of the state of expansion of the lungs and the phase of the cardiac cycle at the time the image was made.

In 514, the canonical impedance image in 512 is used, together with the information on cardiac performance in 506, as input to an algorithm which generates an evaluation of the patient's overall condition, with a view toward determining the optimal treatment in 516. For example, an abnormally high thoracic fluid volume by itself might indicate the need for the patient to take an increased dose of diuretic medication. But some diuretics, such as thiazide, furosemide, and ethacrynic acid, can cause or enhance hypokalemia, which if not treated can lead to arrhythmia. If the ECG data in 506 shows abnormally long QT intervals, especially with prominent U waves, then this by itself might indicate hypokalemia and the need to decrease the dose of diuretics. Only by looking at both ECG data in 506 and impedance imaging in 512, is it possible to determine the optimum dose of medication. An algorithm which uses both ECG data and impedance imaging, and finds the optimum treatment, is optionally based, for example, on experience with the outcomes of other patients with similar combinations of symptoms.

The word "data analyzer" as used herein means any equipment used to analyze data, even if it is not a single unit. For example, when a data analyzer is described as analyzing electrocardiograph data and reconstructing an impedance image, this does not necessarily mean that a single piece of equipment does both the analyzing and the reconstructing. The word "data analyzer" can include one or more ordinary computers running software, one or more pieces of specially designed hardware, or both. The words "comprise", "include" and their conjugates as used herein mean "include but are not necessarily limited to". While the invention has been described with reference to certain exemplary embodiments, various modifications will be readily apparent to and may be readily accomplished by persons skilled in the art without departing from the spirit and scope of the above teachings.

The invention claimed is:

1. A method for generating an impedance image of a subject's chest, comprising:
   acquiring electrical data of the chest;
   formulating an initial impedance image;
   using a finite volume method to calculate an expected set of electrical data if the impedance distribution of the chest matched the initial impedance image;
   determining a difference between the acquired electrical data and the expected electrical data; and
   generating a new impedance image based on said difference;
   wherein generating a new impedance image comprises expressing a Jacobian analytically.

2. A method according to claim 1, wherein calculating an expected set of electrical data and generating a new impedance image are iterated at least one time, using the new impedance image generated in at least one previous iteration to calculate the expected set of electrical data in each iteration except the first iteration.

3. A method according to claim 2, wherein calculating an expected set of electrical data and generating a new impedance image are iterated until the difference between the acquired electrical data and the expected set of electrical data is small enough to satisfy a stopping condition.

4. A method according to claim 1, wherein generating the new impedance image comprises generating with a Newton-Raphson method.

5. A method according to claim 1, wherein generating the new impedance image comprises generating with a modified Newton-Raphson method.

6. A method according to claim 5, wherein generating with a modified Newton-Raphson method comprises adding a regularization matrix to a Hessian matrix.

7. A method according to claim 1, wherein formulating the initial impedance image comprises ascribing typical impedances to different parts of the chest according to at least one image of the chest.

8. A method according to claim 7, wherein ascribing impedances according to at least one image of the chest comprises ascribing impedances according to at least one x-ray image.

9. A method according to claim 8, wherein ascribing impedances according to at least one x-ray image comprises ascribing impedances according to at least one x-ray computed tomography image.

10. A method according to claim 7, wherein ascribing impedance according to at least one image of the chest comprises ascribing impedances according to at least one magnetic resonance image.

11. A method according to claim 7, wherein ascribing impedances according to at least one image of the chest comprises ascribing impedances according to at least one ultrasound image.

12. A method according to claim 1, wherein using the finite volume method comprises inverting a matrix with a technique that is adapted for inverting sparse matrixes.

13. A method according to claim 12, wherein inverting a matrix comprises inverting a matrix with a successive over relaxation method.

14. A method according to claim 1, wherein acquiring electrical data of the chest comprises measuring potentials at a plurality of locations on the subject's body, while known currents are applied at a plurality of locations on the body.

15. An apparatus for making impedance images of a subject's chest, comprising:
   an impedance imaging data acquisition system which acquires impedance imaging data of the chest;
   a data analyzer which reconstructs an impedance image of the chest from said impedance imaging data, using a finite volume method and an analytic Jacobian.

* * * * *